US010799653B2

(12) United States Patent
Biette

(10) Patent No.: US 10,799,653 B2
(45) Date of Patent: Oct. 13, 2020

(54) AEROSOL DELIVERY DEVICE AND METHOD FOR MANUFACTURING AND OPERATING THE SAME

(71) Applicant: United Therapeutics Corporation, Silver Spring, MD (US)

(72) Inventor: Doug Biette, Cary, NC (US)

(73) Assignee: UNITED THERAPEUTICS CORPORATION, Silver Spring, MD (US)

( * ) Notice: Subject to any disclaimer, the term of this patent is extended or adjusted under 35 U.S.C. 154(b) by 0 days.

(21) Appl. No.: 15/401,411

(22) Filed: Jan. 9, 2017

(65) Prior Publication Data

US 2018/0193869 A1    Jul. 12, 2018

(51) Int. Cl.
*B05B 17/06* (2006.01)
*A61M 15/00* (2006.01)
*A61M 11/00* (2006.01)

(52) U.S. Cl.
CPC ...... *A61M 15/0021* (2014.02); *A61M 11/001* (2014.02); *A61M 11/002* (2014.02); (Continued)

(58) Field of Classification Search
CPC ............ B05B 17/0646; B05B 17/0669; A61M 15/0021; A61M 11/005; A61M 11/001; (Continued)

(56) References Cited

U.S. PATENT DOCUMENTS 2,863,075 A    12/1958  Fry
3,360,664 A    12/1967  Straube
(Continued)

FOREIGN PATENT DOCUMENTS

AU    1999959533 B2    2/2000
DE          962296 C    4/1957
(Continued)

OTHER PUBLICATIONS

International Search Report and Written Opinion of the International Searching Authority in PCT/US2017/012685 dated Sep. 18 2017, 15 pages.
(Continued)

*Primary Examiner* — Qingzhang Zhou
(74) *Attorney, Agent, or Firm* — Foley & Lardner LLP

(57) ABSTRACT

An adjustable aerosol delivery device includes an active liquid container, a carrier liquid container, a piezo disc mounted with a flexible gasket relative to the carrier liquid container, an oscillator configured to generate an ultrasonic wave that causes the piezo disc to oscillate and transmit the oscillations through the carrier liquid to the active liquid to cause at least a portion of the active liquid to become an aerosol, a bushing fixed relative to the carrier liquid container via a fixing portion that conforms to and mates with an entire perimeter of a fixing section of the bushing, and a fastener extending through the piezo disc housing and into the bushing. The fastener is configured to be loosened or tightened to manipulate a compression of the gasket to adjust a particle size of the aerosol. A pull force of the bushing is greater than a counter force of the gasket.

7 Claims, 3 Drawing Sheets

(52) U.S. Cl.
CPC ....... *A61M 11/005* (2013.01); *B05B 17/0615* (2013.01); *B05B 17/0669* (2013.01); *A61M 2207/00* (2013.01)

(58) Field of Classification Search
CPC . A61M 2207/00; A61M 15/005; B29C 65/48; B29C 65/70; B29L 2031/7142; B29K 2063/00
USPC .......................... 239/102.2, 102.1, 289, 338
See application file for complete search history.

(56) References Cited

U.S. PATENT DOCUMENTS

| | | | |
|---|---|---|---|
| 3,561,444 A * | 2/1971 | Boucher | A61M 15/0085 128/200.16 |
| 4,001,650 A | 1/1977 | Romain | |
| 4,281,113 A | 7/1981 | Axen et al. | |
| 4,306,075 A | 12/1981 | Aristoff | |
| 4,306,076 A | 12/1981 | Nelson | |
| 4,349,689 A | 9/1982 | Aristoff | |
| 4,473,296 A | 9/1984 | Shofner et al. | |
| 4,486,598 A | 12/1984 | Aristoff | |
| 4,668,814 A | 5/1987 | Aristoff | |
| 4,683,330 A | 7/1987 | Aristoff | |
| 4,692,464 A | 9/1987 | Skuballa et al. | |
| 4,708,963 A | 11/1987 | Skuballa et al. | |
| 5,153,222 A | 10/1992 | Tadepalli et al. | |
| 5,234,953 A | 8/1993 | Crow et al. | |
| 5,363,842 A | 11/1994 | Mishelevich et al. | |
| 5,497,763 A | 3/1996 | Lloyd et al. | |
| 5,514,562 A * | 5/1996 | Saugmann | G01N 21/783 435/23 |
| 5,727,542 A | 3/1998 | King | |
| 5,865,171 A | 2/1999 | Cinquin | |
| 5,881,715 A | 3/1999 | Shibasaki | |
| 5,908,158 A | 6/1999 | Cheiman | |
| 6,054,486 A | 4/2000 | Crow et al. | |
| 6,123,068 A | 9/2000 | Lloyd et al. | |
| 6,357,671 B1 | 3/2002 | Cewers | |
| 6,521,212 B1 | 2/2003 | Cloutier et al. | |
| 6,626,843 B2 | 9/2003 | Hillsman | |
| 6,756,033 B2 | 6/2004 | Cloutier et al. | |
| 6,765,117 B2 | 7/2004 | Moriarty et al. | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 7,544,713 B2 | 6/2009 | Phares et al. | |
| 7,635,094 B2 * | 12/2009 | Chou | B05B 17/0669 239/102.1 |
| 7,726,303 B2 | 6/2010 | Tyvoll et al. | |
| 7,883,031 B2 * | 2/2011 | Collins, Jr. | A61M 11/005 128/200.14 |
| 2003/0192532 A1 | 10/2003 | Hopkins | |
| 2004/0063912 A1 | 4/2004 | Blumberg et al. | |
| 2004/0105819 A1 | 6/2004 | Hale et al. | |
| 2004/0265238 A1 | 12/2004 | Chaudry | |
| 2005/0127198 A1 * | 6/2005 | Brezhnev | B05B 17/0607 239/1 |
| 2005/0165111 A1 | 7/2005 | Wade et al. | |
| 2005/0166913 A1 | 8/2005 | Sexton et al. | |
| 2005/0183719 A1 | 8/2005 | Wuttke et al. | |
| 2005/0282901 A1 | 12/2005 | Phares et al. | |
| 2006/0147520 A1 | 7/2006 | Ruegg | |
| 2006/0201500 A1 | 9/2006 | Von Hollen et al. | |
| 2008/0200449 A1 | 8/2008 | Olschewski et al. | |
| 2008/0280986 A1 | 11/2008 | Wade et al. | |
| 2009/0036465 A1 | 2/2009 | Roscigno et al. | |
| 2010/0076083 A1 | 3/2010 | Olschewski et al. | |
| 2010/0222752 A1 * | 9/2010 | Collins, Jr. | A61M 11/005 604/296 |
| 2010/0282622 A1 | 11/2010 | Phares | |
| 2012/0177693 A1 | 7/2012 | Cipolla et al. | |
| 2012/0216801 A1 | 8/2012 | Olschewski et al. | |
| 2016/0074318 A1 * | 3/2016 | Kamlag | A61K 9/0075 128/203.15 |

FOREIGN PATENT DOCUMENTS

| | | |
|---|---|---|
| DE | 19838711 C1 | 6/2000 |
| DE | 19934582 A1 | 1/2001 |
| FR | 2783431 A1 | 3/2000 |
| JP | 2003-522003 A | 7/2003 |
| WO | WO-01/58514 A1 | 8/2001 |
| WO | WO-01/85241 A1 | 11/2001 |
| WO | WO-2007/028203 A1 | 3/2007 |
| WO | WO-2007/134292 A2 | 11/2007 |

OTHER PUBLICATIONS

Abe et al., "Effects of inhaled prostacyclin analogue on chronic hypoxic pulmonary hypertension," J. Cardiovascular Pharmacology, 2001, 37, 239 251.

Advisory Action dated Jun. 24, 2010 for U.S. Appl. No. 10/978,680, 3 pages).

Agnew JE, Bateman RM, Pavia D, Clarke SW. (1984) Radionuclide demonstration of ventilatory abnormalities in mild asthma. Clinical Science; 66: 525-531.

Annals of the International Commission on Radiological Protection (ICRP) vol. 28, No. 3, 1998, Publication 80, Radiation Dose to Patients from Radiopharmaceuticals.

Aradigm Corporation news release Oct. 24, 2005, "Aradigm and United Therapeutics Sign Development and Commercialization Agreement Targeting Pulmonary Hypertension," Red Orbit News, http://www.redorbit.com/modules/news/tools.php?tool=print&id=281787, 2 pages.

Aristoff et al., "Synthesis of benzopyran prostaglandins, potent stable prostacyclin analogs, via an intermolecular mitsunobu reaction," Tetrahedron Letters, 1984, 25(36):3955-3958.

Bein et al., "Cardiovascular and pulmonary effects of aerosolized prostacyclin administration in severe respiratory failure using a ventilator nebulization system," J. Cardiovascular Pharmacology, 1996, 27, 583-586.

Benedict et al., "Evidence-based pharmacologic management of pulmonary arterial hypertension," Clinical Therapeutics, 2007, 29, 2134-2153.

Bindl et al., "Aerosolised prostacyclin for pulmonary hypertension in neonates," Archives of disease in childhood, Fetal and neonatal edition, 1994, 71(3), F214-6.

Blanchard, J.D., Cipolla, D., Liu, K., Morishige, R., Mudumba, S., Thipphawong, J., Taylor, G., Warren, S., Radhakrishnan, R., Van Vlasselaer, R., Visor , G. and Starko, K. (2003) Lung Deposition of Interferon Gamma-1b following Inhalation via AERx® System vs. Respirgard II™ Nebulizer Proc. ATS Annual Meeting (Abstract A373), Seattle.

Booke et al., "Prostaglandins in Patients with Pulmonary Hypertension: The Route of Administration," Anesth. Analg., 1998, 86:917, Letter to the Editor.

Boyd, B., Noymer, P., Liu, K., Okikawa, J., Hasegawa, D., Warren, S., Taylor, G., Ferguson, E., Schuster, J., Farr, S., and Gonda, I. (2004) Effect of Gender and Device Mouthpiece Shape on Bolus Insulin Aerosol Delivery Using the AERx Pulmonary Delivery System. Pharmaceutical Research. 21 (10) 1776-1782.

Byron, Peter R. "Drug Delivery Devices, Issues in Drug Development," Proc. Am. Thorac. Soc., 2004, 1:321-328.

Channick et al., "Safety and efficacy of inhaled treprostinil as add-on therapy to bosentan in pulmonary arterial hypertension," J. American College of Cardiology, 2006, 48, 1433-1437.

Colthorpe P, Taylor G, Farr SJ. (1997) A comparison of two non-invasive methods for quantifying aerosol deposition in the lungs of rabbits. J. Aerosol Med.; 10:255.

Doyle et al., "Inhaled prostacyclin as a selective pulmonary vasodilator," Anaesthesia and Intensive Care, Aug. 1996, 24(4):514-515.

Dumas et al,. "Hypoxic pulmonary vasoconstriction," General Pharmacology, 1999, 33, 289-297.

(56) References Cited

OTHER PUBLICATIONS

Dworetz et al., "Survival of infants with persistent pulmonary hypertension without extracorporeal membrane oxygenation," Pediatrics, 1989, 84, 1-6.
EPA Integrated Risk Information System (IRIS): data sheet for 3-methylphenol (m-cresol). Accessed at http://www.epa.gov/iris/subst/0301/htm on Mar. 9, 2014.
Espacenet European Patent Office machine translation of Buff et al. DE19934582 (A1), Translation provided on Mar. 8, 2013.
Espacenet European Patent Office machine translation of Gessler et al. DE19838711 (C1), Translation provided on Mar. 8, 2013.
Ewert et al., "Aerosolized iloprost for primary pulmonary hypertension," New England Journal of Medicine, 2000, 343, 1421-1422.
Ewert et al., "Iloprost als inhalative bzw. Intravenose langzeitbehandlung von patienten mit primarer pulmonaler hypertonie," Z. Kardiol., 2000, 89, 987-999, English summary on first page.
Farr et al., "Comparison of in vitro and in vivo efficiencies of a novel unit-dose liquid aerosol generator and a pressurized metered dose inhaler," International Journal of Pharmaceutics, 2000, 198:63-70.
Final Office Action dated Oct. 10, 2014 in U.S. Appl. No. 12/591,200.
Final Office Action dated Oct. 17, 2012 in U.S. Appl. No. 12/591,200.
Final Office Action dated Nov. 4, 2013 in U.S. Appl. No. 12/303,877.
Final Office Action dated Dec. 22, 2011 in U.S. Appl. No. 12/591,200.
Final Office Action dated Mar. 13, 2014 in U.S. Appl. No. 13/469,854.
Final Office Action dated Jul. 2, 2013 in U.S. Appl. No. 13/120,015.
Final Office Action dated Aug. 1, 2012 in U.S. Appl. No. 12/303,877.
Findlay et al., "Radioimmunoassay for the Chemical Stable Prostacyclin Analog, 15AU81: a Preliminary Pharmacokinetics Study in the Dog," Prostaglandins Leukot. Essent. Fatty Acids, Feb. 1993, 48(2):167-174.
Fink et al., "Use of Prostacyclin and its Analogues in the Treatment of Cardiovascular Disease," Heart Disease, 1999, 1:29-40.
Gessler et al., "Ultrasonic versus jet nebulization of iloprost in severe pulmonary hypertension," Eur. Respir. J., 2001, 17, 14-19.
Ghofrani et al., "Hypoxia- and non-hypoxia-related pulmonary hypertension—Established and new therapies," Cardiovascular Research, 2006, 72:30-40.
Haraldsson et al., "Comparison of inhaled nitric oxide and inhaled aerosolized prostacyclin in the evaluation of heart transplant candidates with elevated pulmonary vascular resistance," Chest, 1998, 114, 780-786.
Hoeper et al., "A comparison of the acute hemodynamic effects of inhaled nitric oxide and aerosolized iloprost in primary hypertension," J. American College of Cardiology, 2000, 35, 176-182.
Hoeper et al., "Effects of inhaled nitric oxide and aerosolized iloprost in pulmonary veno-occlusive disease," Respiratory Medicine, 1999, 93, 62-70.
Hoeper et al., "Long term treatment of primary pulmonary hypertension with aerosolized iloprost, a prostacyclin analogue," New England Journal of Medicine, 2000, 342, 1866-1870.
Howarth, P.H., "Why particle size should affect clinical response to inhaled therapy," Journal of Aerosol Medicine, 2001, 14 Supp. 1, S-27-S-34.
Ichida et al., "Additive effects of beraprost on pulmonary vasodilation by inhaled nitric oxide in children with pulmonary hypertension," American Journal of Cardiology, 1997, 80, 662-664.
Krause et al., "Pharmacokinetics and pharmacodynamics of the prostacyclin analogue iloprost in man," Eur. J. Clin. Pharmacol., 1986, 30, 61-68.
Lee et al., "Current strategies for pulmonary arterial hypertension," J. Internal Medicine, 2005, 258, 199-215.
Martin, John C., "Inhaled Form of Remodulin in the Pipeline," http://www.phneighborhood.com/content/in_the_news/archive_2320,aspx, ph Neighborhood, Oct. 28, 2005, 2 pages.
Max et al., "Inhaled prostacyclin in the treatment of pulmonary hypertension," Eur. J. Pediatr., 1999, 158 Suppl 1, S23-S26.
McNulty et al., "The Pharmacokinetics and Pharmacodynamics of the Prostacyclin Analog 15AU81 in the Anesthetized Beagle Dog," Prostaglandins Leukot. Essent. Fatty Acids, Feb. 1993, 48(2):159-166.
Miller et al., "Standardisation of spirometry. Series ATS/ERS Task Force: Standardisation of Lung Function Testing" Eur Respir J 2005; 26: 319-338.
National Radiological Protection Board. Doses to Patients from Medical Radiological Examinations in Great Britain. (1986) Radiological Protection Bulletin No. 77.
Nebu-Tec med. Produkte Eike Kern GmbH, VENTA-NEB®-ir A-I-C-I® Operating Instrutions, Sep. 2005.
Non-Final Office Action dated Jan. 29, 2015 in U.S. Appl. No. 13/120,015.
Non-Final Office Action dated Oct. 11, 2011 in U.S. Appl. No. 12/303,877.
Non-Final Office Action dated Oct. 3, 2012 in U.S. Appl. No. 13/469,854.
Non-Final Office Action dated Oct. 31, 2012 in U.S. Appl. No. 13/120,015.
Non-Final Office Action dated Mar. 13, 2015 in U.S. Appl. No. 13/469,854.
Non-Final Office Action dated Mar. 15, 2013 in U.S. Appl. No. 12/303,877.
Non-Final Office Action dated Mar. 19, 2014 in U.S. Appl. No. 12/591,200.
Notes for Guidance on the Clinical Administration of Radiopharmaceuticals and Use of Sealed Radioactive Sources. Administration of Radioactive Substances Advisory Committee (ARSAC) (Mar. 2006). ARSAC Secretariat, Chilton, Didcot, Oxon. OX11 0RQ.
Office Action dated Dec. 1, 2015, in corresponding Korean Application No. 10-2011-7008976, and English translation, 6 pages.
Olschewski et al. for the German PPH Study Group, "Inhaled iloprost to treat severe pulmonary hypertension—An uncontrolled trial," Annals of Internal Medicine, 2000, 132, 435-443.
Olschewski et al., Aerosolized prostacyclin and iloprost in severe pulmonary hypertension,: Annals of Internal Medicine, 1996, 124, 820 824.
Olschewski et al., "Inhaled prostacyclin and iloprost in severe pulmonary hypertension secondary to lung fibrosis," Am. Respir. Crit. Care Med., 1999, 160, 600-607.
Olschewski et al., "Pharmacodynamics and pharmacokinetics of inhaled iloprost, aerosolized by three different devices, in severe pulmonary hypertension," Chest, 2003, 124, 1294-1304.
Olschewski et al., "Prostacyclin and its analogues in the treatment of pulmonary hypertension," Pharmacology and Therapeutics, 2004, 102, 139-153.
Olschewski et al., "Recovery from circulatory shock in severe primary pulmonary hypertension (PPH) with aerosolization of iloprost," Intensive Care Med., 1998, 24, 631-634.
Pappert et al., "Aerosolized Prostacyclin Versus Inhaled Nitric Oxide in Children with Severe Acute Respiratory Distress Syndrome," Anesthesiology, Jun. 1995, 82(6):1507-1511.
Publications of the International Commission on Radiological Protection (ICRP) (1977) Recommendations of the International Commission on Radiological Protection 26.
Pulmonary Delivery, ONdrugDelivery, 2006, 5 pages.
Rigby, Jonathan, Aradigm Corporation, "Technological advances for success: Product pipeline in targeted pulmonary delivery," Pulmonary Delivery Innovative Technologies Breathing New Life into Inhalable Therapeutics, ONdrugDelivery, http://www.ondrugdelivery.com/publications/Pulmonary.pdf, 2006, 17-19.
Saini et al., "Effect of Electrostatic Charge and Size Distributions on Respirable Aerosol Deposition in Lung Model," Industry Applications Conference, 2004, 39th IAS Annual Meeting, Conference Record of the 2004 IEEE Seattle, WA, Oct. 3-7, 2004, 2:948-952.
Sandifer et al., "Potent effects of aerosol compared with intravenous treprostinil on the pulmonary circulation," J. Appl. Physiol., 2005, 99:2363-2368.
Santak et al., "Prostacyclin aerosol in an infant with pulmonary hypertension," Eur. J. Pediatr., 1995, 154, 233-235.

(56) References Cited

OTHER PUBLICATIONS

Soditt et al., "Improvement of oxygenation induced by aerosolized prostacyclin in a preterm infant with persistent pulmonary hypertension of the newborn," Intensive Care Med., 1997, 23, 1275-1278.
Steffen et al., "The Effects of 15AU81, a Chemically Stable Prostacyclin Analog, on the Cardiovascular and Renin-Angiotensis Systems of Anesthetized Dogs," Prostaglandins, Leukotrienes and Essential Fatty Acids, 1991, 43:277-286.
Stricker et al., "Sustained improvement of performance and haemodynamics with long-term aerosolized prostacyclin therapy in severe pulmonary hypertension," Schweiz Med. Wochenschr., 1999, 129, 923-927.
U.S. Notice of Allowance dated Jun. 11, 2015 in U.S. Appl. No. 12/303,877.
Van Heerden et al., "Inhaled aerosolized prostacyclin as a selective pulmonary vasodilator for the treatment of severe hypertension," Anaesthesia and Intensive Care, 1996, 24, 87-90.
Van Heerden et al., "Re: Delivery of inhaled aerosolized prostacyclin (IAP)," Anaesthesia and Intensive Care, 1996, 24, 624-625.
Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.
Voswinckel et al., "Favorable Effects of Inhaled Treprostinil in Severe Pulmonary Hypertension: Results from Randomized Controlled Pilot Studies" J. Am. Coll. Cardiol., 48(8):1672-1681 (2006).
Voswinckel et al., "Inhaled Treprostinil for Treatment of Chronic Pulmonary Arterial Hypertension," Annals of Internal Medicine, Jan. 17, 2006, 144(2):149-150.
Walmrath et al., "Effects of inhaled versus intravenous vasodilators in experimental pulmonary hypertension," Eur. Respir. J., 1997, 10, 1084-1092.
Wasserman et al., "Bronchodilator effects of prostacyclin (PGI2) in dogs and guinea pigs," European Journal of Pharmacology, 1980, 66, 53-63.
Webb et al., "The use of inhaled aerosolized prostacyclin (IAP) in the treatment of pulmonary hypertension secondary to pulmonary embolism," Intensive Care Med., 1996, 22, 353-355.
Wensel et al., "Effects of iloprost inhalation on exercise capacity and ventilator efficiency in patients with primary pulmonary hypertension," Circulation, 2000, 101, 2388-2392.
Wetzel, R.C., "Aerosolized prostacyclin: in search of the ideal pulmonary vasodilator," Anesthesiology, 1995, 82, 1315-1317.
Wittwer et al., "Inhalative Pre-Treatment of Donor Lungs Using the Aerosolized Prostacyclin Analog Iliprost Ameliorates Reperfusion Injury," J. Heart Lung Transplant, 2005, 24:1673-1679.
Zanen et al., "Optimal particle size for beta 2 agonist and anticholinergic aerosols in patients with severe airflow obstruction," Thorax, 1996, 51, 977-980.
Zanen et al., "The optimal particle size for β-adrenergic aerosols in mild asthmatics," International Journal of Pharmaceutics, 1994, 107, 211-217.

* cited by examiner

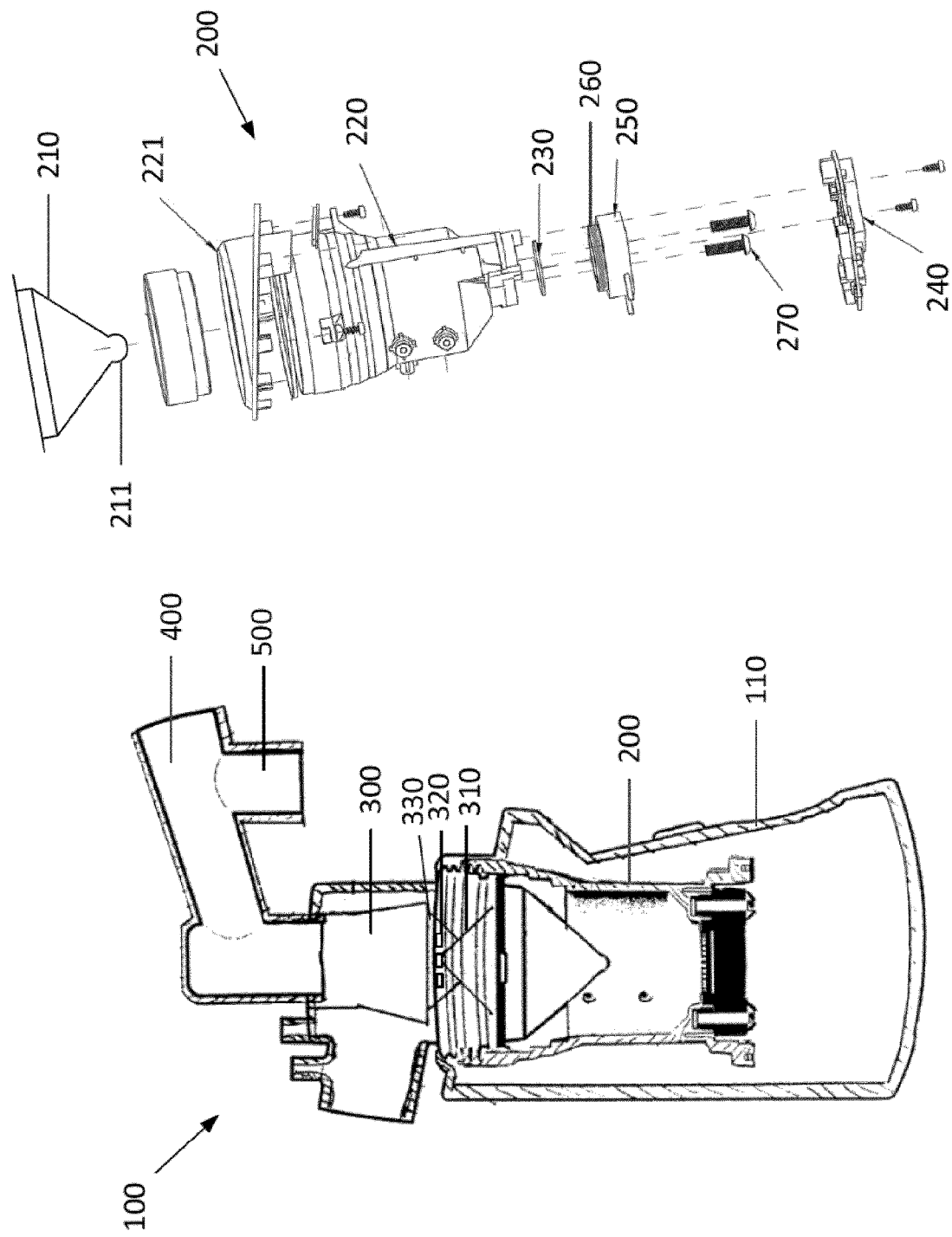

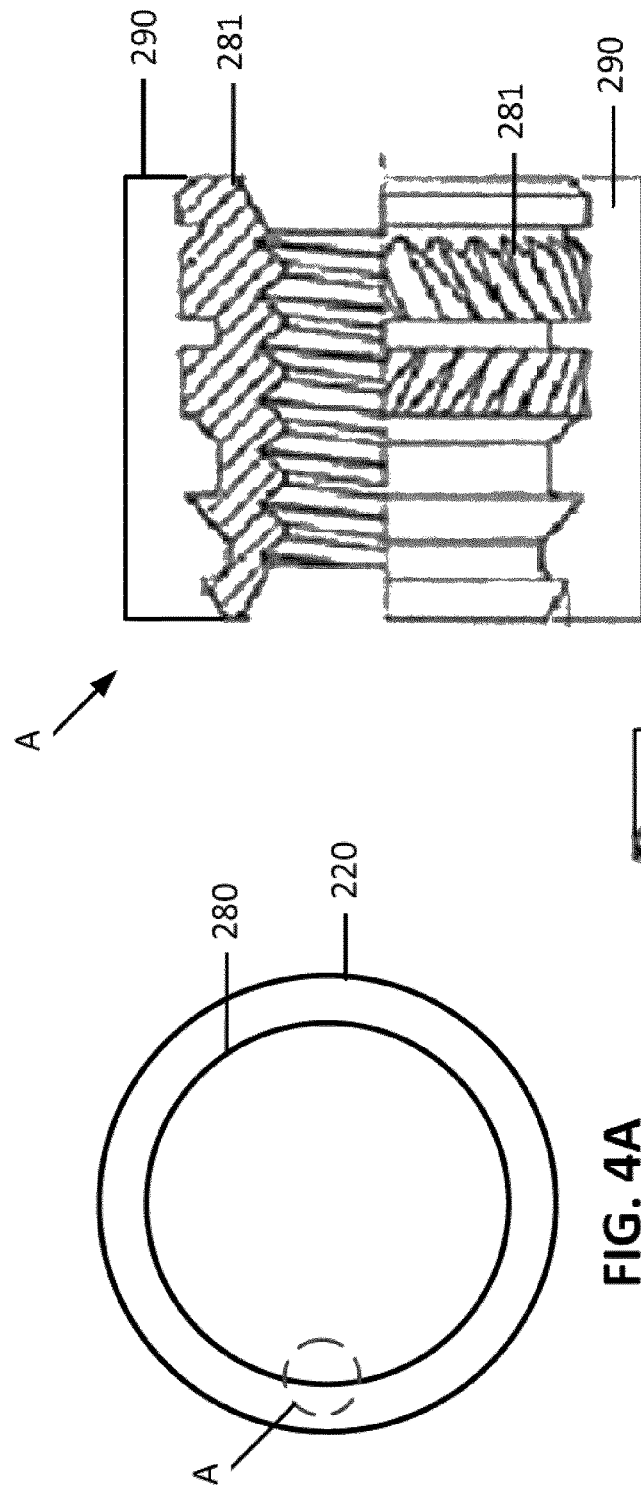
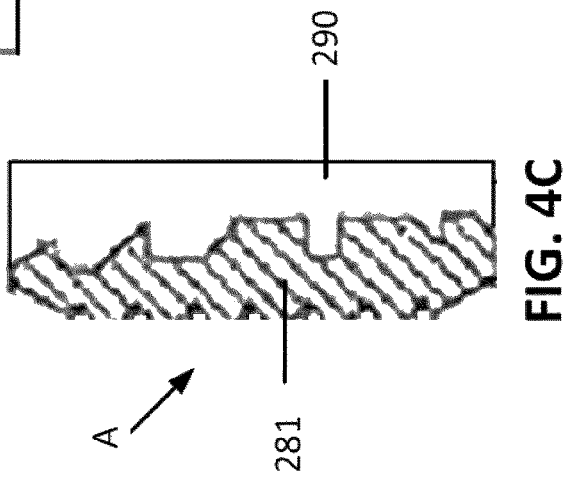
FIG. 4B
FIG. 4C
FIG. 4A

AEROSOL DELIVERY DEVICE AND METHOD FOR MANUFACTURING AND OPERATING THE SAME

FIELD

The present disclosure relates generally to an aerosol delivery device and method for manufacturing and operating the same.

BACKGROUND

Aerosol delivery devices such as nebulizers and inhalers (e.g., a metered dose inhaler) are useful for conveying an active substance in liquid form, together with respiratory air, into the lungs of a user. In particular, the aerosol delivery device transforms a predetermined concentration of an active substance into an aerosol via an atomizer. The aerosol is inhaled by the user into his or her lungs. From the lungs, the active substance is rapidly transferred to the blood stream with low loss.

Variations in blood concentration of a drug can lead to inadequate efficacy if too little drug is present in the blood or at the site of action for any length of time, and to side effects when there is too much drug in the bloodstream or at the site of action. An ideal drug administration modality would achieve a steady concentration of the drug in the "therapeutic window" sufficient to achieve maximum efficacy, while not high enough to engender side effects.

The particle size of an inhaled formulation is an important consideration. Generally, the lungs are designed to exclude particles, so any inhaled formulation must overcome this barrier. The particle size can affect the amount of delivered particles and location of delivery. For example, particles that are too large may not reach deep into lung tissue, and particles that are too small may be exhaled before being deposited and absorbed. Thus, selecting an appropriate particle size and maintaining that particle size are important functions when developing an aerosol delivery device for a pharmaceutical product.

Because an exact dosage of the active substance delivered to the user may vary due to variations in the aerosol particle size, a need exists for improved technology, including a method for delivering a desired aerosol particle size using an aerosol delivery device, where the particle size is controlled, for example, to deliver an accurate dose of the active substance.

SUMMARY

In one embodiment, a method of manufacturing an aerosol delivery device comprises disposing an active liquid container within a carrier liquid container, mounting a piezo disc with a flexible gasket relative to the carrier liquid container, and manipulating a compression of the gasket to adjust a particle size of the aerosol to be produced. The active liquid container is configured to contain an active liquid having an active substance dissolved therein and the carrier liquid container is configured to contain a carrier liquid. The piezo disc is configured to be oscillated by ultrasonic waves generated by an oscillator and transmit the oscillations through the carrier liquid to the active liquid to cause at least a portion of the active liquid to become an aerosol.

In another embodiment, an aerosol delivery device includes an active liquid container configured to contain an active liquid having an active substance dissolved therein, a carrier liquid container configured to receive a carrier liquid, a piezo disc mounted with a flexible gasket relative to the carrier liquid container, wherein the piezo disc is configured to be oscillated by ultrasonic waves generated by an oscillator and transmit the oscillations through the carrier liquid to the active liquid to cause at least a portion of the active liquid to become an aerosol. A method of operating the aerosol delivery device comprises introducing the carrier liquid into the carrier liquid container, introducing the active liquid having the active substance dissolved therein into the active liquid container, inserting the active liquid container into the carrier liquid container such that a portion of the active liquid container is submerged in the carrier liquid, generating an ultrasonic wave with the oscillator that causes the piezo disc to oscillate and transmit the oscillations through the carrier liquid to the active liquid to cause at least a portion of the active liquid to become an aerosol, and manipulating a compression of the gasket to alter a particle size of aerosol.

In yet another embodiment, an adjustable aerosol delivery device comprises an active liquid container configured to contain an active liquid having an active substance dissolved therein, a carrier liquid container configured to receive a carrier liquid, a piezo disc disposed in a piezo disc housing and mounted with a flexible gasket relative to the carrier liquid container, an oscillator configured to generate an ultrasonic wave that causes the piezo disc to oscillate and transmit the oscillations through the carrier liquid to the active liquid to cause at least a portion of the active liquid to become an aerosol, a bushing fixed relative to the carrier liquid container via a fixing portion, the fixing portion conforming to and mating with an entire perimeter of a fixing section of the bushing, and at least one fastener extending through the piezo disc housing and into the bushing. The at least one fastener is configured to be loosened or tightened to manipulate a compression of the gasket to adjust a particle size of the aerosol.

Additional features, advantages, and aspects of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIG. 1 is a front view of a portion of an assembled aerosol delivery device including an active liquid container, a carrier liquid container, a piezo disc housing and an oscillator.

FIG. 2 is an exploded view of the portion of the aerosol delivery device of FIG. 1.

FIG. 4A is a top, cross-sectional view of a bushing fixed relative to a carrier liquid container of the aerosol delivery device of FIG. 1.

FIG. 4B is a side view and a cross-sectional view of a fixing portion engaged with a fixing section of the bushing at a portion A of FIG. 4A.

FIG. 4C is a magnified cross-sectional view of a fixing portion engaged with a fixing section of the bushing at a portion A of FIG. 4A.

DETAILED DESCRIPTION

Figure 3:
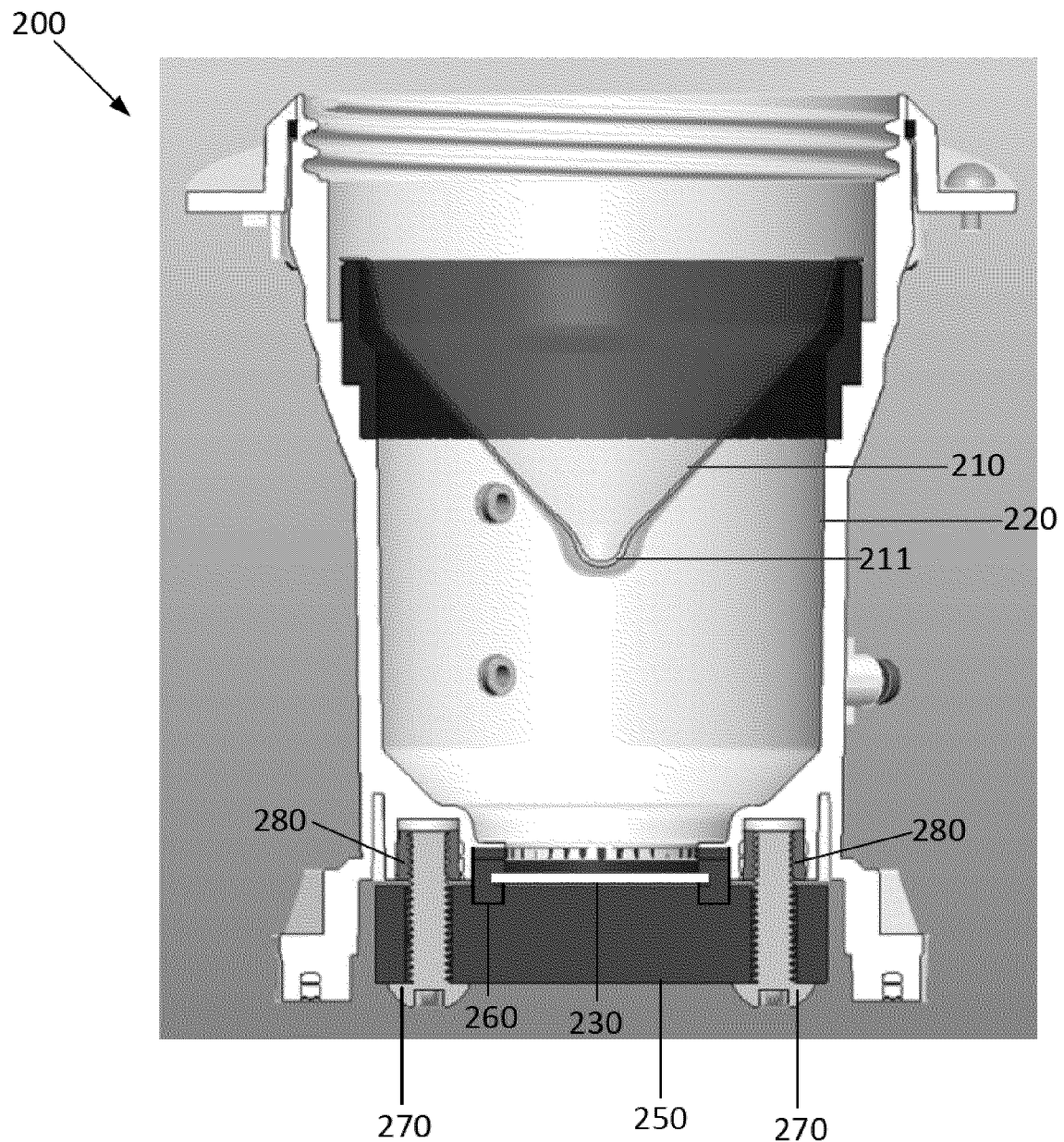
FIG. 3 is an cross-sectional view of a portion of the aerosol delivery device of FIG. 1.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Components of the Aerosol Delivery Device

Referring to FIGS. 1 and 2, an adjustable aerosol delivery device 100, such as a nebulizer or an inhaler, is configured to deliver a liquid having an active substance dissolved therein in aerosol form to a user. The aerosol delivery device 100 also includes an atomizer 200 configured to transform the liquid having the active substance dissolved therein into an aerosol configured to be inhaled by a user. The active substance may be, for example, a medicine configured to be inhaled by a user in the form of an aerosol. The active substance may be used, for example, to treat respiratory conditions. In one embodiment, the active substance can be treprostinil or a pharmaceutically acceptable salt thereof. Treprostinil is approved for the treatment of pulmonary hypertension.

According to a preferred embodiment, the aerosol delivery device 100 may include a dome assembly 300 that connects a mouthpiece, an inhalation piece, and/or a mask 400 to the aerosol delivery device 100. That atomizer 200 (which will be described in detail below) transforms liquid having the active substance dissolved therein into an aerosol configured to be inhaled by a user. The aerosol flows upwards into the dome assembly 300. When a user inhales through the mouthpiece, inhalation piece and/or mask 400, the aerosol within the dome assembly 300 flows upwards and passes through slits 320 in a conical holder 330 of the dome assembly 300 and into the mouthpiece, inhalation piece and/or mask 400. Together, the slits 320 and the conical holder 330 comprise a baffle plate 310.

A particle size of an active substance delivered by the aerosol delivery device 100 may be altered by varying a size (i.e., a width) or number of baffle plates 310 disposed, transverse to the flow, in the interspace between the dome assembly 300 and the active liquid container 210 of the atomizer 200. Varying a width or number of slits 320 alters the size of a gap between the baffle plate 310 and the dome assembly 300 through which the aerosol particles must fit before delivery to the user. In other words, the baffle plates 310 may function similar to a filter.

The aerosol delivery device 100 may optionally include an exhalation port 500 connected to the dome assembly 300. Air exhaled by the user that enters the aerosol delivery device 100, for example, through the mouthpiece, inhalation piece and/or mask 400, may escape through the exhalation port 500. In particular, exhale air within the dome assembly 300 is diverted away from the dome and slits 320 via the exhalation port 500.

According to a preferred embodiment, the atomizer 200 includes an active liquid container 210 configured to receive and contain the liquid having the active substance dissolved therein. The active liquid container 210 may be, for example, a substantially conical active liquid container. The active liquid container 210 is preferably configured and formed of material(s) such that the active liquid container 210 will cause the liquid having the active substance dissolved therein to form an aerosol in response to oscillations generated by an oscillator 240 and transmitted by the carrier liquid, as described below.

According to a preferred embodiment, the atomizer 200 includes a carrier liquid container 220 configured to receive and contain a carrier liquid that can transmit oscillations. The carrier liquid preferably is water and, more preferably, is distilled water. The carrier liquid container 220 is configured to receive the active liquid container 210 in an inverted orientation such that only an apex 211 of the active liquid container 210 is submerged in the carrier liquid disposed in the carrier liquid container 220. The base of the active liquid container 210 is configured to rest, for example, on a flange 221 provided in an interior of the carrier liquid container 220. The atomizer 200 is configured to be received in a device chamber 110 of the aerosol delivery device 100. The device chamber 110 may be a hollow, center portion of the aerosol delivery device 100.

According to a preferred embodiment, the atomizer 200 includes a piezo disc 230. The piezo disc 230 is contained within a piezo disc housing 250 disposed between a base of the carrier liquid container 220 and the oscillator 240. The piezo disc 230 may be, for example, a ceramic disc or a metallic disc. The piezo disc 230 is configured to convert an electrical signal into a mechanical action (i.e., oscillation).

A flexible gasket 260 is provided at a top surface of the piezo disc housing 250 and preferably is configured to mount the piezo disc 230 relative to the carrier liquid container 220 and to seal a space between the mating surfaces of the carrier liquid container 220 and the piezo disc housing 250. As used in regard to the flexible gasket 260, the term flexible means that the gasket is elastic in that the gasket resume its normal shape after being stretched or compressed. In one example, the gasket may have a Shore A value of 35 to 55. In another example, the gasket may have a Shore A value of 40 to 50. In yet another example, the gasket may have an average Shore A value of 45.

The piezo disc housing 250 can be fixed in position relative to the carrier liquid container 220. Preferably, the piezo disc housing 250 is mounted to a base of the carrier liquid container 220 via a bushing 280 fixed within the carrier liquid container 220 and at least one fastener 270 extending through the piezo disc housing 250 and into the bushing 280. The bushing 280 is preferably configured to mate with the fastener 270, e.g., it may be threaded. According to a preferred embodiment, the fastener 270 is configured to be loosened or tightened to manipulate a compression of the flexible gasket 260 to adjust a particle size of the aerosol. By altering a gasket compression, it is possible to achieve particle size distribution equivalence, which allows for the maintenance of emitted dose equivalence. In one experiment, manipulating the gasket compression of the same aerosol delivery device allowed for an alteration in a particle size of the active substance delivered by the aerosol delivery device to be at least in a range of ±0.5 microns.

During operation of the aerosol delivery device 100, some bushings may expand when subjected to the vibrations of the oscillator 240 and/or an increase in temperature associated with the vibrations of the oscillator 240 and then fall back to a relaxed state, for example, when the aerosol delivery device 100 is no longer operated. To prevent the bushing 280 from becoming loose, the bushing 280 is rigidly fixed to the carrier liquid container 220. In particular, the bushing 280 is fixed relative to the carrier liquid container 220 via a fixing portion 290. The fixing portion 290 may be, for example, a knurl such as a straight tooth knurl, an angled knurl, a spiral knurl, a diamond knurl, etc. FIG. 4A illustrates a top, cross-sectional view of the bushing 280 fixed relative to the carrier liquid container 220. FIGS. 4B and 4C illustrate the fixing portion 290 engaging with a fixing section 281 of the bushing 280, for example, at a portion A, disposed at an interface between the carrier liquid container 220 and the bushing 280. The fixing portion 290 conforms to and mates with an entire perimeter of the fixing section 281 of the bushing 280. The fixing section 281 of the bushing 280 may be a partial section of an outer surface area of the bushing 280, an entire outer surface area of the bushing 280, or an entire outer surface area of the bushing 280 excluding a top face and a bottom face of the bushing 280.

In one example, the bushing 280 is insert molded in the fixing portion 290 such that the fixing portion 290 conforms to and mates with an entire perimeter of the fixing section 281 of the bushing 280. In the insert molding process, the bushing 280 is used as an insert placed in a mold, and material is injected into the mold around the bushing 280 and cooled to form the fixing portion 290 and at least a portion of the carrier liquid container 220.

In another example, an insert hole having a diameter larger than a diameter of the bushing 280 is formed at a base of the carrier liquid container 220 in a desired location of the bushing 280. The bushing 280 is inserted into the insert hole and molten plastic or adhesive (e.g., epoxy) is poured into the insert hole between the carrier liquid container 220 and an exterior of the bushing 280 (i.e., molten plastic or adhesive is poured around an exterior of the bushing 280). The plastic or adhesive cures within the insert hole to rigidly hold the bushing 280 in place, as the contours of the exterior of the bushing 280 are filled in with plastic or adhesive. The plastic or adhesive forms the fixing portion 290 that conforms to and mates with the entire perimeter of the fixing section 281 of the bushing 280.

In yet another example, the bushing 280 may be ultrasonically welded to the carrier liquid container 220. The weld forms the fixing portion 290 that conforms to and mates with the entire perimeter of the fixing section 281 of the bushing 280.

Fixing the bushing 280 to the carrier liquid container 220, as described in the examples above, results in the bushing 280 being more rigidly fixed to the carrier liquid container 220 than in a situation in which an insert hole having a diameter substantially the same as a diameter of the bushing is formed in a base of the carrier liquid container, and the bushing is inserted into the insert hole and held in place by friction fit and/or the force of the fastener received in the bushing. Fixing the bushing 280 to the carrier liquid container 220, as described in the examples above, also results in the bushing 280 being more rigidly fixed to the carrier liquid container 220 than in a situation in which an insert hole having a diameter larger than a diameter of the bushing is formed in a base of the carrier liquid container, and the bushing, having a flared design, is inserted into the insert hole and held in place by flared portion of the bushing. As a result, the loosening or relaxation of the bushing over time, which may affect particle size and the dosage of medication delivered by the aerosol device, can be prevented.

The bushing 280 may be selected from any known bushing including a solid sleeve bushing that is solid around a circumference of the bushing, a split bushing that has a cut along a length of the bushing, and clenched bearing that has a cut along a length of the bushing with a clench or cinch traversing the cut, provided that a pull force of the bushing 280 is greater than a counter force of the gasket 260. One of ordinary skill in the art would understand that the pull force of the bushing is the amount of force as measured, for example, by a pull force gauge, required to pull the bushing 280 out of the carrier liquid container 220. For example, the pull force of the bushing may be greater than or equal to 50 pounds. One of ordinary skill in the art would also understand that the counter force of the gasket 260 is a force generated when the gasket 260 is compressed, which is based on a durometer of the gasket 260.

A bearing surface of the bushing 280 may be threaded or smooth. In some embodiments, the bushing 280 may be formed of a rigid material, for example, metallic materials, such as at least one of brass, aluminum, copper, bronze, steel, or stainless steel. As used in regard to the bushing 280, the term rigid means that it has a stiffness, k, greater than or equal to a predetermined stiffness. For example, the predetermined bushing stiffness may be in the kN range. Stiffness, k, can be determined by the equation k=F/δ; where F is the force applied on the body; and δ is the displacement produced by the force along the same degree of freedom. In some embodiments, the bushing 280 may be a metallic bushing or a bi-metallic bushing. In other embodiments, the bushing 280 may be a plastic bushing. In additional embodiments, the bushing 280 may be formed of multiple materials, e.g., plastic encased within a metal shell. The bushing 280 may be formed of any material, as long as the pull force of the bushing 280 is greater than the counter force of the gasket 260. Although the bushing 280 is rigidly fixed to the carrier liquid container 220, one of ordinary skill in the art would understand that the mounting of the piezo disc housing 250 to the base of the carrier liquid container 220 is flexible and adjustable by changing the torque of the at least one fastener 270.

The fastener 270 is preferably configured to mate with the bushing 280, e.g., it may be threaded. The fastener 270 is preferably a bolt that can be threaded into the bushing 280. In some embodiments, the fastener 270 may be formed of a rigid material, for example, metallic materials, such as at least one of brass, aluminum, copper, bronze, steel, or stainless steel. As used in regard to the fastener 270, the term rigid means that it has a stiffness, k, greater than or equal to a predetermined stiffness. For example, the predetermined fastener stiffness may be in the kN range. Stiffness, k, can be determined by the equation k=F/δ; where F is the force applied on the body; and δ is the displacement produced by the force along the same degree of freedom. The fastener 270 may be formed of any material that provides the desired rigidity. For example, any material may be selected, so long as the material exceeds the pull force of the bushing 280 (e.g., the 50 pound force described above). Typically, metallic materials, such as at least one of brass, aluminum, copper, bronze, steel, or stainless steel, will provide the desired rigidity. For example, the fastener 270 may be a M12 stainless steel screw with tension/shear capacities in the kN range. The fastener 270 may be formed of multiple materials, e.g., plastic encased within a metal shell, as long as it provides the desired rigidity at the area of contact with the bushing 280.

In one embodiment, the aerosol delivery device 100 includes an oscillator 240 that is configured to generate an ultrasonic wave that causes the piezo disc 230 to oscillate and transmit the oscillations through the carrier liquid to the active liquid to cause at least a portion of the active liquid to become an aerosol. The oscillator 240 can be configured to have a desired frequency, which preferably is at least or nominally 2.4 MHz. The oscillator 240 can have a single oscillating element or can be comprised of a plurality of oscillating elements, having a net frequency that equals the desired frequency, e.g., at least or nominally 2.4 MHz. The mechanical vibration of the piezo disc 230 generates a mist on the surface of the liquid in the active liquid container 220, which separates the liquid in the active liquid container 210 into an aerosol, which is a mixture of air and particles of the active substance. The particle size of the active substance is very small. For example, when the active substance is treprostinil, a distribution of the particle size is centered on 2 microns. In some embodiments, the particle size may be 4 microns or less, in particular, 2 to 4 microns.

Methods for Altering a Particle Size of the Active Substance Delivered by the Aerosol Delivery Device It may be desirable to manufacture an aerosol delivery device that can be manipulated to deliver the same active substance with different particle sizes.

In one embodiment (described in detail below), a particle size of the same active substance delivered by the same aerosol delivery device 100 is altered by manipulating a mean compression of the gasket 260. Increasing the mean compression of the gasket 260 allows the atomizer 200 to produce smaller particle sizes of the same active substance, while decreasing the compression of the gasket 260 allows the atomizer 200 to produce larger particle sizes of the same active substance. In some instances, it is preferable to produce smaller particle sizes of the active substance. The mean compression of the gasket 260 may be altered, for example, by loosening or tightening the at least one fastener 270 that mounts the piezo disc housing 250 to the base of the carrier liquid container 220.

The bushing 280 of the aerosol delivery device 100 remains rigid whether or not the aerosol delivery device 100 is operating. This rigidity allows for a more accurate compression of the gasket 260. Although the bushing 280 is rigid, one of ordinary skill in the art would understand that the mounting of the piezo disc housing 250 to the base of the carrier liquid container 220 is flexible and adjustable by changing the torque of the at least one fastener 270. By changing the torque of the at least one fastener 270, a pressure exerted on the gasket 260 may be finely controlled. The mean compression of the gasket 260 may be altered, for example, in a range from 0.1 to 1.0 mm, in particular, from 0.5 to 0.7 mm, and even more particularly from 0.51 to 0.66 mm.

It is believed that altering the mean compression of the gasket 260 alters translation of an energy focal point when comparing aerosol delivery devices having the same torque specifications of the fastener 270. Altering the mean compression of the gasket 260 is believed to alter the proportion of energy directed into the liquid of the carrier liquid container 220 versus the energy directed into the piezo disc housing 250 (including the piezo disc 230 and the gasket 260). The fastener 270 may be loosened or tightened to achieve a desired amount of rigidity between the carrier liquid container 220 and the piezo disc housing 250 via the bushing 280 in which the fastener 270 is mounted. It is preferable to tighten the fastener 270, but leave the fastener 270 loose enough such that a predetermined minimum proportion of the energy is delivered to the piezo disc housing 250 and absorbed by the gasket 260. If the fastener 270 is over-tightened (i.e., over-torqued), the connection of the piezo disc housing 250 to the base of the carrier liquid container 220 may become rigid, and all of the energy may be delivered to the liquid of the carrier liquid container 220, thereby causing the piezo disc 230 to crack if ceramic. If the piezo disc 230 is metallic, the piezo disc 230 may fail due to loss of piezo material on the disc. Altering the mean compression of the gasket 260 may also alter the resonant frequency of the piezo disc 230. In addition, because the gasket 260 constrains motion at the edge of the piezo disc 230, altering the mean compression of the gasket 260 may also change the mechanical load. For at least these reasons, altering the mean compression of the gasket 260 by loosening or tightening the fastener 270 will allow for a change in particle size of the active substance delivered from the mask or the mouthpiece of the aerosol delivery device 100.

Other alternatives may be used to adjust the particle size of the active substance delivered by the aerosol delivery device 100, provided that a net actuation frequency of the oscillator 240 is at least 2.4 MHz and the mounting of the piezo disc housing 250 to the base of the active liquid container 220 is flexible.

As one alternative, the carrier liquid container 220 itself may be threaded, either as part of the molding process or by using plastic cutting screws. In this embodiment, the bushing 280 is eliminated such that the fastener 270 is directly inserted into an insert hole formed in a base of the carrier liquid container 220.

As another alternative, the material of the gasket 260 may be changed to one having a stiffer or a softer durometer. Even if the same force is applied by the fastener 270, using a gasket 260 having a different material would change the compression force.

Manufacturing the Aerosol Delivery Device

A method for manufacturing an aerosol delivery device 100 includes disposing the atomizer 200 and the dome assembly 300 at least partially within the device chamber 110 and inserting the mouthpiece, inhalation piece and/or mask 400 into the dome assembly 300. The method includes disposing the active liquid container 210 within the carrier liquid container 220, providing the piezo disc 230 within the piezo disc housing 250, mounting the piezo disc housing 250 to a base of the carrier liquid container 220, sealing a space between the mating surfaces of the carrier liquid container 220 and the piezo disc housing 250 with a gasket 260, and providing an oscillator 240 at a base of the piezo disc housing 250. The oscillator 240 is configured to generate an ultrasonic wave that causes the piezo disc 230 to vibrate and separate the liquid in the active liquid container 210 into an aerosol containing air and particles of the active substance. The method of manufacturing the aerosol delivery device 100 further includes manipulating a compression of the gasket 260 to alter a particle size of the active substance that the aerosol delivery device 100 is configured to produce. Increasing the compression of the gasket reduces the particle size of the active substance that the aerosol delivery device is configured to produce.

As seen in FIG. 3, in one embodiment, the piezo disc housing 250 is mounted to the base of the carrier liquid container 220 using at least one fastener 270 that is received in a bushing 280 rigidly fixed to the carrier liquid container 220, for example, by insert molding. The bushing 280 may be selected from any known bushing including a solid sleeve bushing that is solid around a circumference of the bushing, a split bushing that has a cut along a length of the bushing, and clenched bearing that has a cut along a length of the bushing with a clench or cinch traversing the cut. The bushing 280 may be a metallic bushing, a bi-metallic bushing, or a plastic bushing. In the embodiments in which the bushing 280 is a metallic bushing or a bi-metallic bushing, the bushing 280 may be made, for example, from brass, aluminum, copper, bronze, steel, or stainless steel. In at least one embodiment, the bushing 280 is not a plastic bushing.

The method of manufacturing the aerosol delivery device 100 may further include altering at least one of an orientation of the piezo disc 230 within the piezo disc housing 250 and an orientation of the gasket 260 within the piezo disc housing 250 to further alter the particle size of the active substance that the aerosol delivery device 100 is configured to produce.

The method of manufacturing the aerosol delivery device 100 may further include altering a calibration of the aerosol delivery device 100 to further alter the particle size of the active substance that the aerosol delivery device 100 is configured to produce. Altering a calibration of the aerosol delivery device 100 may be done as an alternative to, or in addition to altering at least one of an orientation of the piezo disc 230 within the piezo disc housing 250 and an orientation of the gasket 260 within the piezo disc housing 250 to further alter the particle size of the active substance that the aerosol delivery device 100 is configured to produce.

Operating the Aerosol Delivery Device

A method of operating the aerosol delivery device 100 includes introducing the carrier liquid into the carrier liquid container 220, introducing the liquid having the active substance dissolved therein into the active liquid container 210, inserting the active liquid container 210 into the carrier liquid container 220 such that a portion of the active liquid container 210 is submerged in the carrier liquid, generating an ultrasonic wave with the oscillator 240 that causes the piezo disc 230 to oscillate and transmit the oscillations through the carrier liquid to the active liquid to cause at least a portion of the active liquid to become an aerosol, and manipulating a compression of the gasket 260 to alter a particle size of the active substance produced by the aerosol delivery device 100.

The method of operating the aerosol delivery device 100 further includes increasing the compression of the gasket 260 to reduce the particle size of the active substance produced by the aerosol delivery device 100. The compression of the gasket 260 may be manipulated by loosening or tightening the at least one fastener 270 used to mount the piezo disc housing 250 to the base of the carrier liquid container 220.

The method of operating the aerosol delivery device 100 may further include altering at least one of an orientation of the piezo disc 230 within the piezo disc housing 250 and an orientation of the gasket 260 within the piezo disc housing 250 to further alter the particle size of the active substance produced by the aerosol delivery device 100.

The method of operating the aerosol delivery device 100 may further include altering a calibration of the aerosol delivery device 100 to further alter the particle size of the active substance produced by the aerosol delivery device 100. Altering the calibration of the aerosol delivery device 100 may be done as an alternative to or in addition to altering at least one of an orientation of the piezo disc 230 within the piezo disc housing 250 and an orientation of the gasket 260 within the piezo disc housing 250 to further alter the particle size of the active substance produced by the aerosol delivery device 100.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary aspects, and that such variations are intended to be encompassed by the present disclosure.

It is important to note that the construction and arrangement of the aerosol delivery device as shown in the various exemplary aspects are illustrative only. Although only a few aspects have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative aspects. Other substitutions, modifications, changes and omissions may also be made in the design, operating conditions and arrangement of the various exemplary aspects without departing from the scope of the present invention.

What is claimed:

1. A method of operating an aerosol delivery device including an active liquid container configured to contain an active liquid having an active substance dissolved therein, a carrier liquid container configured to receive a carrier liquid, a piezo disc mounted relative to the carrier liquid container by a flexible gasket, and a piezo disc housing disposed between a base of the carrier liquid container and an oscillator, wherein the piezo disc is mounted relative to the carrier liquid container by inserting at least one fastener through the piezo disc housing, wherein the piezo disc is configured to be oscillated by ultrasonic waves generated by the oscillator and transmit oscillations through the carrier liquid to the active liquid to cause at least a portion of the active liquid to become an aerosol, the method comprising:
    introducing the carrier liquid into the carrier liquid container;
    introducing the active liquid having the active substance dissolved therein into the active liquid container;
    inserting the active liquid container into the carrier liquid container such that a portion of the active liquid container is submerged in the carrier liquid;
    generating an ultrasonic wave with the oscillator that causes the piezo disc to oscillate and transmit the oscillations through the carrier liquid to the active liquid to cause at least the portion of the active liquid to become the aerosol; and manipulating a compression of the flexible gasket via the piezo disc housing to alter a particle size of the aerosol by adjusting the at least one fastener inserted through the piezo disc housing to mount the piezo disc housing relative to the carrier liquid container.

2. The method of claim 1, wherein manipulating the compression of the flexible gasket includes increasing the compression of the flexible gasket to reduce the particle size of the aerosol or decreasing the compression of the flexible gasket to increase the particle size of the aerosol.

3. The method of claim 1, wherein mounting the piezo disc relative to the active liquid container further includes inserting the at least one fastener through the piezo disc housing and into a bushing fixed within the carrier liquid container, and wherein a pull force of the bushing is greater than a counter force of the flexible gasket.

4. The method of claim 3, wherein fixing the bushing relative to the carrier liquid container comprises providing a contoured surface that conforms to and mates with an entire perimeter of a fixing section of the bushing to fix the bushing relative to the carrier liquid container.

5. The method of claim 4, wherein fixing the bushing relative to the carrier liquid container comprises insert molding the contoured surface such that the contoured surface conforms to and mates with the entire perimeter of the fixing section of the bushing.

6. The method of claim 4, wherein fixing the bushing relative to the carrier liquid container comprises:

providing an insert hole in the base of the carrier liquid container, the insert hole having a diameter greater than a diameter of the bushing;

inserting the bushing into the insert hole; and introducing adhesive material into the insert hole between an exterior surface of the bushing and the carrier liquid container, the adhesive material conforming to and mating with the entire perimeter of the fixing section of the bushing.

7. The method of claim 3, wherein manipulating the compression of the flexible gasket comprises loosening or tightening the at least one fastener.

\* \* \* \* \*